United States Patent
Youn et al.

(10) Patent No.: US 9,877,948 B2
(45) Date of Patent: Jan. 30, 2018

(54) ROTIGOTINE-CONTAINING TRANSDERMAL ABSORPTION PREPARATION WITH IMPROVED STABILITY

(71) Applicant: SK Chemicals Co., Ltd., Seongnam-si (KR)

(72) Inventors: Wonno Youn, Seoul (KR); Yeo-Jin Park, Seoul (KR); Hun-Teak Kim, Seoul (KR)

(73) Assignee: SK Chemicals Co., Ltd., Seongnam-si (KR)

( * ) Notice: Subject to any disclaimer, the term of this patent is extended or adjusted under 35 U.S.C. 154(b) by 0 days.

(21) Appl. No.: 15/354,716

(22) Filed: Nov. 17, 2016

(65) Prior Publication Data

US 2017/0128413 A1   May 11, 2017

Related U.S. Application Data

(63) Continuation of application No. PCT/KR2015/005045, filed on May 20, 2015.

(30) Foreign Application Priority Data

May 21, 2014   (KR) .................. 10-2014-0061193

(51) Int. Cl.
| | |
|---|---|
| *A61K 31/381* | (2006.01) |
| *A61K 9/00* | (2006.01) |
| *A61K 9/70* | (2006.01) |
| *A61K 47/22* | (2006.01) |

(52) U.S. Cl.
CPC .......... *A61K 31/381* (2013.01); *A61K 9/0014* (2013.01); *A61K 9/7053* (2013.01); *A61K 47/22* (2013.01)

(58) Field of Classification Search
None
See application file for complete search history.

(56) References Cited

U.S. PATENT DOCUMENTS

| | | | |
|---|---|---|---|
| 7,413,747 B2 | 8/2008 | Muller et al. | |
| 8,211,462 B2 | 7/2012 | Breitenbach et al. | |
| 8,246,979 B2 | 8/2012 | Schacht et al. | |
| 8,545,872 B2 | 10/2013 | Breitenbach | |
| 2005/0033065 A1 | 2/2005 | Mueller et al. | |
| 2008/0131494 A1 | 6/2008 | Reed et al. | |
| 2010/0086582 A1 | 4/2010 | Tang et al. | |
| 2011/0027345 A1* | 2/2011 | Wang ............... | A61K 9/7053 424/448 |
| 2011/0066120 A1* | 3/2011 | Lee ................... | A61F 13/02 604/290 |
| 2011/0165247 A1 | 7/2011 | Breitenbach | |
| 2012/0322845 A1 | 12/2012 | Wolff et al. | |
| 2015/0118309 A1 | 4/2015 | Kim et al. | |

FOREIGN PATENT DOCUMENTS

| | | |
|---|---|---|
| EP | 1033978 | 9/2000 |
| EP | 1769785 | 4/2007 |
| KR | 10-2005-0038007 | 4/2005 |
| KR | 10-2005-0056942 | 6/2005 |
| KR | 10-2005-0086373 | 8/2005 |
| KR | 10-2011-0082142 | 7/2011 |
| KR | 10-2014-0006729 | 1/2014 |
| WO | 9949852 | 10/1999 |
| WO | 2011/076879 | 6/2011 |

OTHER PUBLICATIONS

International Search Report dated Aug. 12, 2015 in International Application No. PCT/KR2015/005045.

* cited by examiner

*Primary Examiner* — Robert A Wax
*Assistant Examiner* — Quanglong N Truong
(74) *Attorney, Agent, or Firm* — H.C. Park & Associates, PLC

(57) ABSTRACT

A method for preparing a transdermal absorption composition includes mixing rotigotine and an antioxidant at a weight ratio of 1:0.0001 to 0.1. A transdermal therapeutic system includes a substrate and a drug-containing adhesive layer disposed on the substrate and including an antioxidant at a weight ratio of 1:0.0001 to 0.1. The method and system of the present invention suppress the crystallization of rotigotine as well as the generation of related substances, thereby increasing the long-term storage stability of a therapeutic product containing rotigotine or related substances.

17 Claims, 3 Drawing Sheets

[FIG. 1]
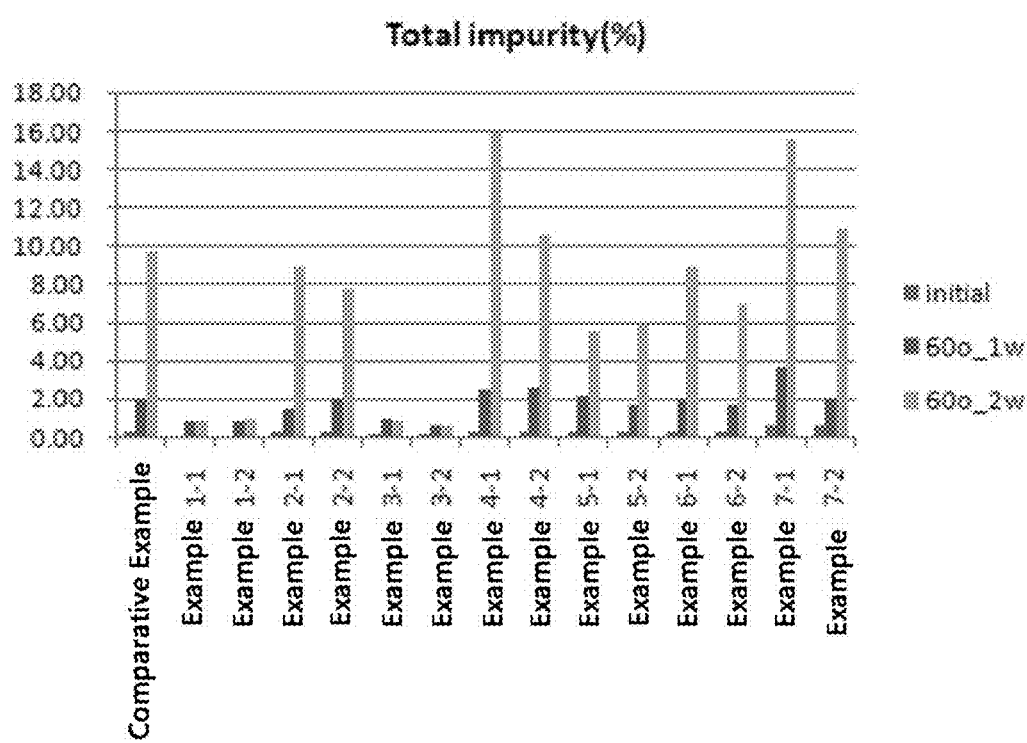

[FIG. 2]
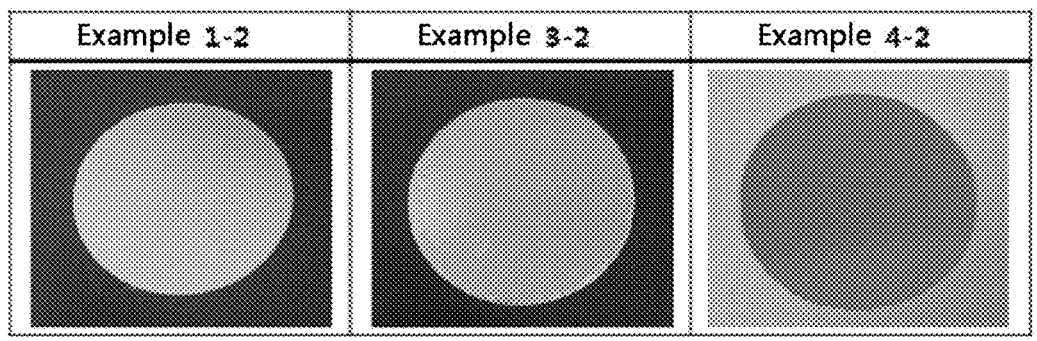

[FIG. 3]
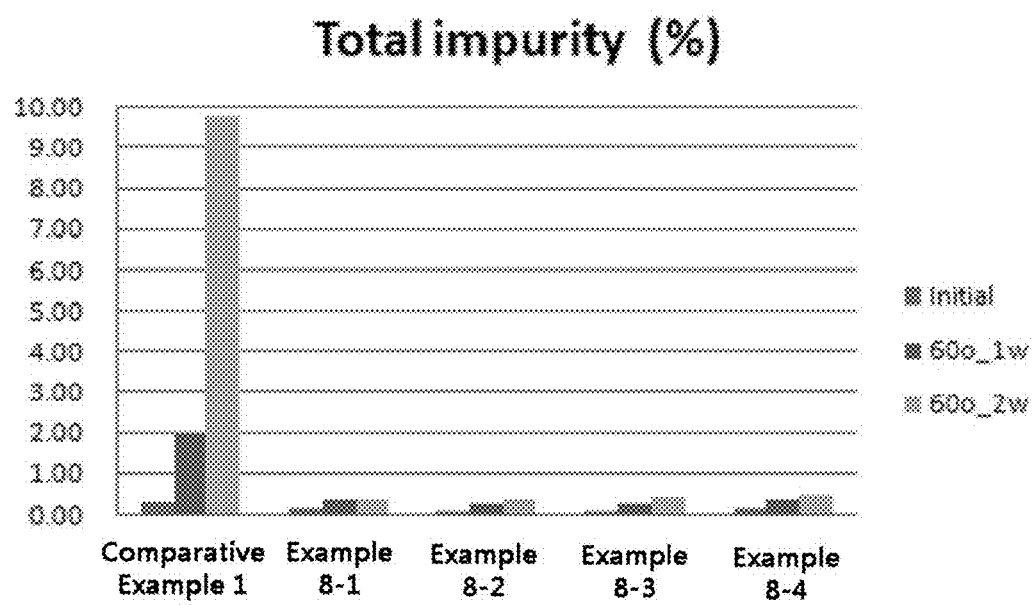

ROTIGOTINE-CONTAINING TRANSDERMAL ABSORPTION PREPARATION WITH IMPROVED STABILITY

CROSS-REFERENCE TO RELATED APPLICATIONS

This application is a Continuation of International Patent Application No. PCT/KR2015/005045, filed on May 20, 2015, and claims priority from and the benefit of Korean Patent Application No. 10-2014-0061193, filed on May 21, 2014, each of which is incorporated by reference for all purposes as if fully set forth herein.

BACKGROUND

Field

The present invention relates to a method for preventing the crystal precipitation of rotigotine in a composition for transdermal absorption containing rotigotine as an active ingredient, and more specifically, to a method for preparing a composition for transdermal absorption, the method comprising mixing rotigotine and an antioxidant at a weight ratio of 1:(0.0001-0.1); to a transdermal absorption preparation prepared by the method; and to a transdermal therapeutic system comprising a drug-containing adhesive layer containing rotigotine and an antioxidant at a weight ratio of 1:(0.0001-0.1), and a substrate for supporting the drug-containing adhesive layer.

Discussion of the Background

Rotigotine, (−)-5,6,7,8-tetrahydro-6-[propyl-[2-(2-thienyl)ethyl]amino]-1-naphtahlenol, is used as a non-ergoline dopamine agonist for the treatment of Parkinson's disease (PD) and restless legs syndrome (RLS).

Rotigotine has been commercially available as a transdermal patch. A transdermal patch having a rotigotine composition is disclosed in U.S. Pat. No. 7,413,747B. Also, a commercially available rotigotine patch employs a silicone adhesive, which is disclosed in EP 1033978B. However, the commercially available patch causes the precipitation of crystals of rotigotine under room-temperature storage conditions, and thus it is difficult to secure the storage period necessary for commercial distribution of such a patch. In order to solve the problem, WO 2011/076879 discloses a rotigotine transdermal composition with a polymer (such as polyvinylpyrrolidone) added thereto, but the use of such an additive may degrade the stability of rotigotine. In addition, the addition of a crystal precipitation inhibitor for preventing the crystal precipitation of rotigotine may degrade the transmittance of rotigotine. Thus, EP 1769785 discloses the use of a transmittance promoter, but the use of the transmittance promoter may also cause the destabilization of rotigotine. In order to solve the above problems, measures for stabilizing active materials have been continuously studied.

SUMMARY

While researching methods for preventing the crystal precipitation of rotigotine from a rotigotine patch preparation and improving storage stability thereof, the present inventors unexpectedly found that, in mixing rotigotine and an antioxidant at a particular ratio, merely the treatment with the antioxidant caused no crystal formation of rotigotine, and then completed the present invention.

Therefore, an aspect of the present invention is to provide a method for preparing a transdermal absorption composition (or preparation used throughout the application), the method comprising mixing rotigotine and an antioxidant at a weight ratio of 1:(0.0001-0.1).

Another aspect of the present invention is to provide a transdermal absorption preparation prepared by the method.

Still another aspect of the present invention is to provide a transdermal therapeutic system comprising: a drug-containing adhesive layer containing rotigotine and an antioxidant at a weight ratio of 1:(0.0001-0.1), and a substrate for supporting the drug-containing adhesive layer.

Still further another aspect of the present invention is to provide a method for preventing the crystallization of rotigotine, the method comprising mixing rotigotine and an antioxidant at a weight ratio of 1:(0.0001-0.1).

In accordance with an aspect of the present invention, there is provided a method for preparing a transdermal absorption preparation, the method comprising mixing rotigotine and an antioxidant at a weight ratio of 1:(0.0001-0.1).

In accordance with another aspect of the present invention, there is provided a transdermal absorption preparation prepared by the method of the present invention.

In accordance with still another aspect of the present invention, there is provided a transdermal therapeutic system comprising: a drug-containing adhesive layer containing rotigotine and an antioxidant at a weight ratio of 1:(0.0001-0.1), and a substrate for supporting the drug-containing adhesive layer.

In accordance with further still another aspect of the present invention, there is provided a method for preventing the crystallization of rotigotine, the method comprising mixing rotigotine and an antioxidant at a weight ratio of 1:(0.0001-0.1).

BRIEF DESCRIPTION OF THE DRAWINGS

FIG. 1 illustrates the results of testing a reduction effect of impurity according to the type and content of an antioxidant in the present invention. (Comparative Example 1: antioxidant non-addition group, Example 1-1: ascorbic acid addition group (API: antioxidant=1:0.1), Example 1-2: ascorbic acid addition group (API: antioxidant=1:0.03), Example 2-1: DL-α-tocopherol addition group (API: antioxidant=1:0.1), Example 2-2: DL-a-tocopherol addition group (API: antioxidant=1:0.03), Example 3-1: ascorbyl palmitate addition group (API: antioxidant=1:0.1), Example 3-2: ascorbyl palmitate addition group (API: antioxidant=1:0.03), Example 4-1: 2,5-dihydroxybenzoic acid addition group (API: antioxidant=1:0.1), Example 4-2: 2,5-dihydroxybenzoic acid addition group (API: antioxidant=1:0.03), Example 5-1: propyl gallate addition group (API: antioxidant=1:0.1), Example 5-2: propyl gallate addition group (API: antioxidant=1:0.03), Example 6-1: butylated hydroxytoluene addition group (API: antioxidant=1:0.1), Example 6-2: butylated hydroxytoluene addition group (API: antioxidant=1:0.03), Example 7-1 butylated hydroxyanisole addition group (API: antioxidant=1:0.1), Example 7-2: butylated hydroxyanisole addition group (API: antioxidant=1:0.03)).

FIG. 2 illustrates the crystal precipitation results of a transdermal absorption preparation when ascorbic acid was added as an antioxidant (Example 1-2), when 2,5-dihydroxybenzoic acid was added as an antioxidant (Example 4-2), and when ascorbyl palmitate was added as an antioxidant (Example 3-2).

FIG. 3 illustrates results of testing a reduction effect of impurity according to the content of ascorbic acid.

DETAIL DESCRIPTION OF THE ILLUSTRATED EMBODIMENTS

Hereinafter, the present invention will be described in detail.

However, the following examples are merely for illustrating the present invention and are not intended to limit the scope of the present invention.

The present invention provides a method for preparing a transdermal absorption composition (or preparation used throughout the application), the method comprising mixing rotigotine and an antioxidant at a weight ratio of 1:(0.0001-0.1).

The rotigotine ((−)-5,6,7-tetrahydro-6-[propyl-[2-(2-thienyl)ethyl]amino]-1-naphtahlenol) has a structure of Chemical Formula 1 below, and is used for the treatment of Parkinson's disease (PD) and restless legs syndrome (RLS) as a non-ergoline dopamine agonist. The rotigotine in the present invention includes a compound represented by Chemical Formula 1 below and a salt thereof.

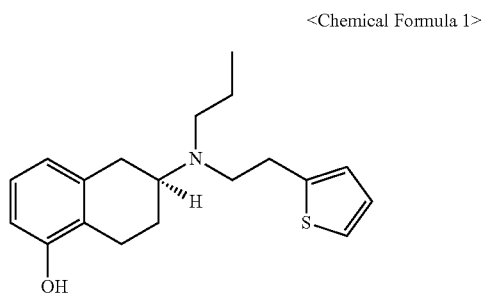 [SMILES: CCCN(CCc1cccs1)[C@H]1CCc2c(O)cccc2C1]

<Chemical Formula 1>

As used herein, the antioxidant refers to a material which delays or inhibits the oxidation of a substrate while existing in a small quantity compared with the substrate. The antioxidant in the present invention is not limited as long as it has an antioxidative action or antioxidative synergistic action. For example, the antioxidant may be at least one selected from the group consisting of a tocopherol and an ester thereof, ascorbic acid, ascorbyl palmitate, 2,5-dihydroxybenzoic acid, butylated hydroxytoluene, butylated hydroxyanisole, and propyl gallate.

The reference documents, US 2011/0165247, WO 2012/084, etc., disclose that an antioxidant may be added, as a selective option or additive feature, to a patch or a transdermal absorption preparation containing rotigotine as an active ingredient. However, the documents merely suggest that the antioxidant may be added for the purpose of preventing the oxidation of a product. However, the present invention has rotigotine and an antioxidant as major essential ingredients, and it is first established in the present invention that the antioxidant alone has an effect of preventing the crystal precipitation of rotigotine.

The antioxidant according to the present invention improves the storage stability of rotigotine and prevents the crystal precipitation of rotigotine. Thus, any material that improves the storage stability of rotigotine, prevents the crystal precipitation of rotigotine, and has an antioxidative effect may be used without limitation. For example, the antioxidant may be at least one selected from the group consisting of a tocopherol and an ester thereof, ascorbic acid, ascorbyl palmitate, 2,5-dihydroxybenzoic acid, butylated hydroxy toluene, butylated hydroxyanisole, and propyl gallate. The antioxidant of the present invention may preferably be a water-soluble antioxidant, and more preferably, 2,5-dihydroxybenzoic acid and ascorbic acid.

The amount of the antioxidant mixed with rotigotine is not particularly limited, but the weight ratio of the rotigotine to the antioxidant may be preferably 1:(0.0001-0.1), and more preferably 1:(0.001-0.1). The addition of less than 0.0001 parts by weight of the antioxidant may be highly likely to decrease the effect of the antioxidant, while the addition of more than 0.1 parts by weight of the antioxidant may cause severe skin toxicity, resulting in another side effect.

The method of the present invention can be applied to prepare various dosage forms containing rotigotine as an active ingredient, and may preferably be applied to prepare a patch, a liquid, an ointment, an oral agent, and the like.

In an example of the present invention, rotigotine patches (transdermal preparations) containing rotigotine were prepared by mixing rotigotine with a tocopherol and an ester thereof, ascorbic acid, ascorbyl palmitate, 2,5-dihydroxybenzoic acid, butylated hydroxytoluene, butylated hydroxyanisole, propyl gallate, and the like, followed by testing the improvement in stability of rotigotine. Each of the prepared patches was put on a Petri dish and then stored in 60° C. strict test conditions (for one week and two weeks), and as a result, it was verified that the amount of impurity generated was significantly reduced compared with a comparative example without an antioxidant added thereto. Especially, it was verified that the effect of reducing impurity was excellent in test groups with ascorbic acid and ascorbyl palmitate added thereto. That is, the antioxidants effectively reduce an increase in the impurity of rotigotine, thereby making it possible to prepare a rotigotine-containing patch with high long-term storage stability. The term "impurity" means total impurity. Ascorbic acid and ascorbyl palmitate reduced an increase in total impurity, while reducing especially (s)-6-(2-(Thiophen-2-yl)ethylamino)-5,6,7,8-tetrahydronaphthalen-1-ol, which is the impurity generated from rotigotine by photolysis, oxidation, heat, or the like.

In another example of the present invention, rotigotine patches were prepared by mixing ascorbic acid at several proportions, followed by testing for the improvement in stability of rotigotine. The results showed less than approximately 0.5% of total impurity at any ascorbic acid proportion, and thus verified that the storage stability was highly improved by containing ascorbic acid.

In another example of the present invention, a patch prepared by adding ascorbic acid or ascorbyl palmitate as an antioxidant was tested for the crystal precipitation of rotigotine. The prepared patch was put on a Petri dish, and stored in acceleration test conditions of 40° C. and relative humidity of 60% (for two weeks). The crystal precipitation was observed by the naked eye visualization, and photographed through a digital camera. The results verified that a transdermal absorption preparation containing an antioxidant, ascorbic acid, caused no crystals even in room-temperature distribution.

According to the preparation method of the present invention, it was verified that merely a treatment with an antioxidant alone, without polyvinyl pyrrolidone and crystal precipitation inhibitors, which were conventionally used for the prevention of crystal precipitation of rotigotine, prevented the crystal precipitation of rotigotine and caused little impurity, leading to a rotigotine transdermal absorption preparation possessing an excellent long-term storage ability. Especially, specific antioxidants, such as ascorbic acid and 2,5-dihydroxybenzoic acid, have an excellent effect in preventing the crystal precipitation of rotigotine.

Therefore, the present invention provides a transdermal absorption preparation prepared by the method of the present invention.

The transdermal absorption preparation of the present invention is prepared by a method comprising mixing rotigotine and an antioxidant at a weight ratio of 1 (0.0001-0.1). The ratio of rotigotine to the antioxidant in the present invention is described as in the above method for preparing a transdermal absorption preparation.

The transdermal absorption preparation of the present invention contains rotigotine as an active drug ingredient, allows convenient administration of the drug into the human body in a skin patch manner, and can constantly sustain its pharmaceutical effect for a long time. In addition, the increase in impurity is greatly reduced during the storage of rotigotine by containing an antioxidant as an active ingredient, and the rotigotine is not crystallized by mixing antioxidant with rotigotine at a particular ratio, leading to its stable storage for a long time. The rotigotine and the antioxidant, which are the active ingredients of the transdermal absorption preparation of the present invention, are described above.

The transdermal absorption preparation of the present invention may further contain an adhesive in addition to rotigotine and an antioxidant.

The adhesive allows the transdermal absorption preparation of the present invention to be in continuous contact with the skin and thus facilitate the absorption of active ingredients. It may include an acryl-based adhesive, a rubber-based adhesive, an ethylene-vinyl acetate adhesive, a styrene-based adhesive, and a silicone-based adhesive. More preferably, the adhesive of the present invention may be a styrene-based adhesive. The term "styrene-based adhesive" refers to an adhesive containing a styrene-based block copolymer as a base material. The styrene-based block copolymer may be at least one block copolymer selected from the group consisting of styrene-isoprene, styrene-butadiene, styrene-isoprene-styrene, styrene-butadiene-styrene, styrene-isoprene-styrene-styrene, and styrene-butadiene-styrene-butadiene, but is not limited thereto. The styrene-based adhesive of the present invention may be, most preferably, polyisobutylene, while an adhesive product well known in the art, for example, Durotak 87-6911 (Henkel), may be commercially purchased and used.

The adhesive of the present invention is preferably contained at a ratio of 40-500 parts by weight per 10 parts by weight of rotigotine.

In addition, the transdermal absorption preparation of the present invention may further contain a crystal precipitation inhibitor. The crystal precipitation inhibitor prevents the crystal precipitation of rotigotine during the storage of rotigotine and thus increases the storage stability of rotigotine for a long time. For example, at least one crystal precipitation inhibitor selected from the group consisting of a fatty alcohol, a fatty acid, a fatty acid ester, a fatty acid amide, and a derivative thereof may be used.

In addition, the transdermal absorption preparation may further contain a solubilizer capable of dissolving rotigotine.

The solubilizer is used to completely dissolve rotigotine when a transdermal absorption preparation is prepared. Examples of the solubilizer may include: hydrophilic organic solvents, such as propylene glycol, diethylene glycol monobutyl ether, diproptylene glycol, polyethylene glycol, polypylene glycol monocaprylate, and tripropylene glycol; aprotic solvents, such as dimethyl sulfoxide; and pyrrolidones, such as 1-vinyl-2-pyrrolidone and n-methyl pyrrolidone.

In addition, the transdermal absorption preparation of the present invention may further contain a skin permeation promoter, an excipient, an abirritant, a stabilizer or a carrier.

The skin permeation promoter is used to promote the permeation of a drug into the skin, and examples thereof may include hydrophilic organic solvents, aprotic solvents, fatty acids, fatty alcohols, fatty acid esters, pyrrolidones, essential oil, surfactants, and phospholipids.

The stabilizer is an agent for preventing the separation of a drug. As a stabilizer contained in the transdermal absorption preparation of the present invention, a pharmaceutically acceptable alkalifying agent or an antioxidant that is ordinarily used may be used. Examples of an acceptable stabilizer may include, but are not limited to, butylated hydroxytoluene (BHT), dibutyl hydroxy toluene (DHT), butylated hydroxyanisole (BHA), sodium sulfite, sodium pyrosulfite, sodium hydrogen sulfite, benzoic acid sodium, sodium metabisulfite, propyl gallate, calcium phosphate, a tocopherol and its ester, and the like.

The carrier contained in the transdermal absorption preparation of the present invention is a biocompatible carrier, and may include, but is not limited to, a carrier for parenteral administration. The carrier for parenteral administration may include water, appropriate oil, saline solution, aqueous glucose, glycol, and the like. The following literature may be referred to for other examples of the pharmaceutically acceptable carrier (Remington's Pharmaceutical Sciences, 19th ed., Mack Publishing Company, Easton, Pa., 1995). The concentration of the biocompatible carrier may be, but is not limited to, about 2-70 wt %.

The transdermal absorption preparation according to the present invention may be formulated into a patch, a liquid, an ointment, or the like, and may preferably be formulated into a patch.

Meanwhile, the present invention provides a transdermal therapeutic system comprising: a drug-containing adhesive layer containing rotigotine and an antioxidant at a weight ratio of 1:(0.0001-0.1); and a substrate for supporting the drug-containing adhesive layer.

The transdermal therapeutic system of the present invention comprises: a drug-containing adhesive layer containing rotigotine and an antioxidant at a weight ratio of 1:(0.0001-0.1); and a substrate for supporting the drug-containing adhesive layer. The transdermal therapeutic system has an effect of treating diseases, such as Parkinson's disease and restless legs syndrome, through the skin permeation of rotigotine.

The drug-containing adhesive layer of the present invention contains rotigotine as an active drug ingredient, an antioxidant for preventing the crystallization of rotigotine, and an adhesive, wherein the rotigotine and the antioxidant are contained at a weight ratio of 1:(0.0001-0.1).

The ratio of rotigotine to the antioxidant in the transdermal therapeutic system of the present invention is described as in the method for preparing a transdermal absorption preparation.

As used herein, the rotigotine, antioxidant, and adhesive are described above.

In the drug therapeutic system of the present invention, the content of the antioxidant is not particularly limited, but may be 0.0001 or more and 0.1 or less parts by weight on the basis of 1 part by weight of rotigotine. The addition of less than 0.0001 parts by weight of the antioxidant may be highly likely to decrease the antioxidative effect of the antioxidant, while the addition of more than 0.1 parts by weight of the antioxidant may cause severe skin irritation, resulting in another side effect.

In the drug-containing adhesive layer of the present invention, the ratio of the rotigotine, the antioxidant, and the adhesive is not particularly limited, while the weight ratio of the rotigotine, the antioxidant, and the adhesive may be preferably 1:(0.0001-0.1):(4-50). More preferably, the proportion of the antioxidant may be 0.001-0.01.

In cases where the proportion of the adhesive is lower than the above numerical range, the adhesive strength decreases and thus the drug-containing adhesive layer does not favorably adhere to the skin. On the contrary, in cases where the proportion of the adhesive is higher than the above numerical range, the drug-containing adhesive layer adheres to the skin too tightly, and thus when a drug delivery system is attached to and detached from the skin, the skin may be irritated and the drug release may be delayed.

The transdermal therapeutic system of the present invention comprises a substrate for supporting the drug-containing adhesive layer. For the substrate, any substrate that can be used for the known patches or the like may be used. Preferably, any substrate that is thin and flexible, has no reactivity with the drug-containing adhesive layer and the skin and thus causes no allege response may be used as the substrate of the present invention. For example, a non-woven fabric, polyethylene terephthalate, soft polyvinylchloride, polyurethane, polyester, a silicone coating film, or an aluminum film may be used as the substrate of the present invention. Preferably, a silicone coating film, an aluminum film, or polyethylene terephthalate (PET) may be used.

In the transdermal therapeutic system of the present invention, the content of rotigotine may vary depending on the age, body weight, and gender of a patient, the manner of administration, the health condition, and the severity of a disease. For instance, it may be applied once a day or divided into multiple doses such that 0.5-100 mg of the active material can be administered.

In an example of the present invention, a drug-containing adhesive layer was formed by mixing rotigotine, ethanol, N-methyl pyrrolidone, an antioxidant, and polyisobutylene (here, a nucleic acid is optionally added according to a test group). The drug-containing adhesive layer was coated on a silicone coating film, and then bonded with a PET film, thereby preparing a transdermal therapeutic system, which was then tested for stability thereof by storing in strict conditions for 1 week or 2 weeks. The results verified that the impurity of rotigotine was greatly increased in a control group not containing an antioxidant, whereas the generation of impurity was insignificant in the transdermal therapeutic system of the present invention.

The present invention provides a method for preventing the crystal precipitation of rotigotine, the method comprising mixing rotigotine and an antioxidant at a weight ratio of 1:(0.0001-0.1).

The contents of the rotigotine and antioxidant in the "method for preventing the crystal precipitation of rotigotine" are described as in the "method for preparing a transdermal absorption preparation". The method of the present invention may be applied to various dosage forms containing rotigotine as an active ingredient, and may preferably be applied to a patch, a liquid, an ointment, an oral agent, and the like.

The present invention provides a method for preparing a transdermal absorption preparation, the method comprising mixing rotigotine and an antioxidant at a weight ratio of 1:(0.0001-0.1), a transdermal absorption preparation prepared by the method, and a transdermal therapeutic system comprising: a drug-containing adhesive layer containing rotigotine and an antioxidant at a weight ratio of 1:(0.0001-0.1); and a substrate for supporting the drug-containing adhesive layer. The method, preparation, and system of the present invention suppress the generation of impurity of rotigotine and inhibit the crystallization of rotigotine, thereby increasing its long-term storage stability, and thus can be effectively applied to the preparation of a rotigotine-containing patch.

Example 1

Preparation and Crystallization Evaluation of Patch Containing Antioxidant

Rotigotine transdermal preparations were prepared by adding a total of seven types of antioxidants following Table 1 below (API represents a raw drug, that is, rotigotine).

TABLE 1

| Classification | Antioxidant |
| --- | --- |
| Comparative Example 1 | No addition |
| Example 1-1 | Ascorbic acid(API:antioxidant = 1:0.1) |
| Example 1-2 | Ascorbic acid(API:antioxidant = 1:0.03) |
| Example 2-1 | DL-α-tocopherol(API:antioxidant = 1:0.1) |
| Example 2-2 | DL-α-tocopherol(API:antioxidant = 1:0.03) |
| Example 3-1 | Ascorbyl palmitate (API:antioxidant = 1:0.1) |
| Example 3-2 | Ascorbyl palmitate (API:antioxidant = 1:0.03) |
| Example 4-1 | 2,5-Dihydroxybenzoic acid (API:antioxidant = 1:0.1) |
| Example 4-2 | 2,5-Dihydroxybenzoic acid (API:antioxidant = 1:0.03) |
| Example 5-1 | Propyl gallate(API:antioxidant = 1:0.1) |
| Example 5-2 | Propyl gallate(API:antioxidant = 1:0.03) |
| Example 6-1 | Butylated hydroxytoluene (API:antioxidant = 1:0.1) |
| Example 6-2 | Butylated hydroxytoluene (API:antioxidant = 1:0.03) |
| Example 7-1 | Butylated hydroxyanisole (API:antioxidant = 1:0.1) |
| Example 7-2 | Butylated hydroxyanisole (API:antioxidant = 1:0.03) |

In Comparative Example 1, 300 mg of rotigotine, 400 mg of ethanol, and 200 mg of n-methyl pyrrolidone were mixed to completely dissolve rotigotine, and then 1 g of hexane was added thereto, thereby preparing a homogenous solution. In Examples 1-1, 2-1, 3-1, 4-1, 5-1, 6-1, and 7-1, 300 mg of rotigotine, 400 mg of ethanol, 200 mg of n-methyl pyrrolidone, and 30 mg of an antioxidant were mixed to completely dissolve rotigotine, and then 1 g of hexane was added thereto, thereby preparing a homogenous solution. In Examples 1-2, 2-2, 3-2, 4-2, 5-2, 6-2, and 7-2, 300 mg of rotigotine, 400 mg of ethanol, 200 mg of n-methyl pyrrolidone, and 10 mg of an antioxidant were mixed to prepare a homogenous solution. To each of these solutions, 4.2 g of a styrene-based adhesive (product name: Durotak 87-6911 (Henkel)) was added, followed by mixing at 600 rpm or higher for 10 minutes, thereby preparing a transdermal absorption preparation. Each of the prepared transdermal absorption preparations was allowed to stand at room temperature, thereby allowing bubbles to burst. After the removal of bubbles was confirmed, the mixture without bubbles (transdermal absorbable preparation) was coated on a silicone coating film such that rotigotine can be contained in 0.4-0.5 mg per unit area (1 $cm^2$), and then a polyester (PET) film or aluminum film was bonded thereto, thereby preparing a patch. The prepared transdermal administration system (patch) was molded into a 10 cm²-circle, which was put on a Petri dish, and then stored in 60° C. strict test conditions (for 1 week, 2 weeks). The degree of generation of impurity was measured through high-performance liquid chromatography (HPLC).

As test results, as shown in FIG. 1, when exposed to the strict environment for 2 weeks, the amount of generation of impurity of rotigotine increased to 8% for 2 weeks in the Comparative Example without an antioxidant, whereas the impurity of less than 1% was generated in Examples 1 and 3 with ascorbic acid and ascorbyl palmitate added. The term "impurity" means total impurity. Ascorbic acid and ascorbyl palmitate reduced the increase in total impurity, respectively, and especially, reduced (s)-6-(2-(Thiophen-2-yl)ethyl-amino)-5,6,7,8-tetrahydronaphthalen-1-ol, which is an impurity generated from rotigotine by photolysis, oxidation, heat, or the like.

Example 2

Crystallization Evaluation

The degree of crystallization of rotigotine was measured according to the type of antioxidant.

Each of the patches prepared by the methods in Examples 1-2 and 3-2, showing the smallest amount in the generation of impurity in Example 1, was molded into a 10 cm²-circle, and then put on a Petri dish, and stored in acceleration test conditions of 40° C. and relative humidity of 60% (for two weeks). The crystal precipitation was observed by the naked eye visualization, and photographed through a digital camera.

As test results, as shown in FIG. 2, no crystals were formed in the transdermal absorption preparation of Example 1-2 with ascorbic acid as an antioxidant and the transdermal absorption preparation of Example 4-2 with 2,5-dihydroxybenzoic acid as an antioxidant, whereas a plurality of crystals were precipitated in the transdermal absorption preparation of Example 3-2 with ascorbyl palmitate as an antioxidant. It was verified that the transdermal abruption preparation containing ascorbic acid or 2,5-dihydroxybenzoic acid caused no formation of crystals even in the room-temperature distribution, leading to a great improvement in storage convenience.

Example 3

Preparation and Evaluation of Patch According to the Content of Ascorbic Acid

Rotigotine transdermal preparations were prepared according to a total of five contents of ascorbic acid as described in the following Table 2.

TABLE 2

| Classification | Content of Ascorbic acid | Ascorbic acid proportion (%) relative to entire preparation |
|---|---|---|
| Comparative Example 1 | API:ascorbic acid = 1:0 | 0 |
| Example 8-1 | API:ascorbic acid = 1:0.003 | 0.05 |
| Example 8-2 | API:ascorbic acid = 1:0.010 | 0.16 |
| Example 8-3 | API:ascorbic acid = 1:0.017 | 0.26 |
| Example 8-4 | API:ascorbic acid = 1:0.033 | 0.52 |

The preparation method was the same as in Example 1. Each of the prepared transdermal administration systems (patches) was molded into a 10 cm²-circle, and then put on a Petri dish, and stored in 60° C. strict test conditions (for two weeks). The degree of generation of impurity was measured through high-performance liquid chromatography (HPLC).

As shown in FIG. 1 and FIG. 3, when exposed to the strict environment for 2 weeks, the amount of generation of total impurity showed about 9.76% in Comparative Example 1 without ascorbic acid, whereas the generation of total impurity of less than about 0.5% was showed in Examples 8-1 to 8-4 with any proportion of ascorbic acid. Therefore, it can be concluded that the storage stability of the transdermal systems was significantly improved by containing ascorbic acid.

INDUSTRIAL APPLICABILITY

As set forth above, the present invention relates to a method for preventing the crystal precipitation of rotigotine in a transdermal absorption preparation containing rotigotine as an active ingredient, and more specifically, provides a method for preparing a transdermal absorption preparation, the method comprising mixing rotigotine and an antioxidant at a weight ratio of 1:(0.0001-0.1), a transdermal absorption preparation prepared by the method, and a transdermal therapeutic system comprising: a drug-containing adhesive layer containing rotigotine and an antioxidant at a weight ratio of 1:(0.0001-0.1); and a substrate for supporting the drug-containing adhesive layer. The method and system of the present invention are highly industrially applicable since they reduce the generation of impurity of rotigotine and inhibit the crystallization of rotigotine, thereby increasing the long-term storage stability and being effectively applied to the preparation of a rotigotine-containing patch.

The invention claimed is:

1. A method for preparing a transdermal absorption composition, the method comprising mixing rotigotine and an antioxidant at a weight ratio of 1:(0.0001-0.1),
    wherein the method excludes mixing rotigotine with polyvinylpyrrolidone.

2. The method of claim 1, wherein the rotigotine and the antioxidant are mixed at a weight ratio of 1:(0.001-0.1).

3. The method of claim 1, wherein the antioxidant comprises a material selected from the group consisting of tocopherol, an ester of tocopherol, ascorbic acid, ascorbyl palmitate, 2,5-dihydroxybenzoic acid, butylated hydroxytoluene, butylated hydroxyanisole, propyl gallate, and some combination thereof.

4. The method of claim 1, wherein the antioxidant comprises a compound selected from the group consisting of ascorbic acid, 2,5-dihydroxybenzoic acid, and some combination thereof.

5. A transdermal absorption composition prepared by the method of claim 1.

6. A transdermal therapeutic system comprising:
    a substrate the drug-containing adhesive layer; and
    a drug-containing adhesive layer disposed on the substrate and comprising rotigotine and an antioxidant,
    wherein the transdermal therapeutic system excludes polyvinylpyrrolidone.

7. The transdermal therapeutic system of claim 6, wherein the drug-containing adhesive layer comprises the rotigotine and the antioxidant at a weight ratio of 1:(0.001-0.1).

8. The transdermal therapeutic system of claim 6, wherein the antioxidant comprises a material selected from the group consisting of tocopherol, an ester of tocopherol, ascorbic acid, ascorbyl palmitate, 2,5-dihydroxybenzoic acid, butylated hydroxytoluene, butylated hydroxyanisole, propyl gallate, and combination thereof.

9. The transdermal therapeutic system of claim 6, wherein the antioxidant comprises a compound selected from the group consisting of ascorbic acid, 2,5-dihydroxybenzoic acid, and some combination thereof.

10. The transdermal therapeutic system of claim 6, wherein the adhesive comprises adhesive composition selected from the group consisting of a silicone-based adhesive, a rubber-based adhesive, an acryl-based adhesive, an ethylene-vinyl acetate based adhesive, and some combination thereof.

11. The transdermal therapeutic system of claim 10, wherein the rubber-based adhesive comprises a styrene-based adhesive.

12. A method for preventing the crystallization of rotigotine, the method comprising mixing rotigotine and an antioxidant at a weight ratio of 1:(0.0001-0.1), wherein the method excludes mixing rotigotine with polyvinylpyrrolidone.

13. The transdermal therapeutic system of claim 6, wherein the drug-containing adhesive layer comprises the rotigotine and the antioxidant at a weight ratio of 1:(0.0001-0.1).

14. The transdermal therapeutic system of claim 13, wherein the transdermal therapeutic system is a transdermal therapeutic patch.

15. The method of claim 1, wherein the antioxidant is 2,5-dihydroxybenzoic acid.

16. The transdermal therapeutic system of claim 6, wherein the antioxidant is 2,5-dihydroxybenzoic acid.

17. The method of claim 12, wherein the antioxidant is 2,5-dihydroxybenzoic acid.

* * * * *